(12) United States Patent
Anderson et al.

(10) Patent No.: US 7,691,645 B2
(45) Date of Patent: Apr. 6, 2010

(54) IMMUNOSUBTRACTION METHOD

(75) Inventors: N. Leigh Anderson, Washington, DC (US); Rembert Pieper, Washington, DC (US)

(73) Assignee: Agilent Technologies, Inc., Santa Clara, CA (US)

(*) Notice: Subject to any disclaimer, the term of this patent is extended or adjusted under 35 U.S.C. 154(b) by 780 days.

(21) Appl. No.: 09/977,358

(22) Filed: Oct. 16, 2001

(65) Prior Publication Data

US 2002/0127739 A1 Sep. 12, 2002

Related U.S. Application Data

(60) Provisional application No. 60/260,217, filed on Jan. 9, 2001.

(51) Int. Cl.
G01N 33/543 (2006.01)

(52) U.S. Cl. ............... 436/518; 436/513; 530/412; 530/413

(58) Field of Classification Search ............... 435/7.1, 435/7.92, 174, 287.1, 287.2, 288.6, 962, 435/973, 287.8, DIG. 15, DIG. 16, DIG. 35, 435/DIG. 36, DIG. 40, DIG. 45, DIG. 48; 436/518–542, 161, 175, 177, 178; 530/413; 422/59–60, 69–70, 101

See application file for complete search history.

(56) References Cited

U.S. PATENT DOCUMENTS

| | | | | |
|---|---|---|---|---|
| 3,710,933 A * | 1/1973 | Fulwyler et al. | ............... | 209/3.1 |
| 4,427,653 A | 1/1984 | Springer | ............... | 424/85 |
| 4,708,931 A * | 11/1987 | Christian | ............... | 435/7.92 |
| 4,722,896 A | 2/1988 | Kadish | ............... | 435/68 |
| 5,137,808 A * | 8/1992 | Ullman et al. | ............... | 435/7.9 |
| 5,372,783 A | 12/1994 | Lackie | ............... | 422/68.1 |
| 5,639,440 A | 6/1997 | Martin, Jr. | ............... | 424/9.2 |
| 5,670,134 A | 9/1997 | Martin, Jr. | ............... | 424/9.2 |
| 5,879,881 A * | 3/1999 | Rubenstein | ............... | 435/5 |
| 5,993,627 A | 11/1999 | Anderson et al. | ............... | 204/456 |
| 5,998,222 A | 12/1999 | Weimer | ............... | 436/518 |
| 6,225,047 B1 * | 5/2001 | Hutchens et al. | ............... | 435/5 |
| 6,228,624 B1 * | 5/2001 | Terstappen | ............... | 435/173.9 |
| 6,235,503 B1 * | 5/2001 | Lindemann et al. | ............... | 435/91.2 |
| 6,379,665 B1 | 4/2002 | Frohman et al. | ............... | 424/94.6 |
| 6,399,317 B1 | 6/2002 | Weimer | ............... | 435/7.2 |
| 6,410,692 B2 | 6/2002 | Stevens | ............... | 530/388.25 |
| 6,455,263 B2 * | 9/2002 | Payan | ............... | 435/7.1 |
| 6,459,994 B1 | 10/2002 | Parekh et al. | ............... | 702/19 |

(Continued)

FOREIGN PATENT DOCUMENTS

JP    09-033504    2/1997

(Continued)

OTHER PUBLICATIONS

Stausbol-Gron, B. et al. A model phage display subtraction method with potential for analysis of differential gene expression. FEBS Letters. 1996;391:71-75.*

(Continued)

Primary Examiner—Christopher L Chin

(57) ABSTRACT

Removal of abundant proteins from a sample enhances detection and resolution of less abundant proteins in the sample such as in two-dimensional gel electrophoresis. The removal is accomplished by immunosubtraction of several high abundance, interfering or contaminating proteins simultaneously.

22 Claims, 7 Drawing Sheets

U.S. PATENT DOCUMENTS

| | | | |
|---|---|---|---|
| 6,539,102 B1 | 3/2003 | Anderson et al. | 382/128 |
| 6,602,502 B1 | 8/2003 | Strahilevitz | |
| 6,632,655 B1* | 10/2003 | Mehta et al. | 435/288.5 |
| 6,649,419 B1* | 11/2003 | Anderson | 436/526 |
| 6,696,304 B1* | 2/2004 | Davies | 436/518 |
| 2001/0051380 A1 | 12/2001 | Stevens | |
| 2002/0028005 A1 | 3/2002 | Anderson et al. | |
| 2003/0032017 A1 | 2/2003 | Anderson et al. | |
| 2003/0186329 A1* | 10/2003 | Madison et al. | 435/7.1 |
| 2004/0072251 A1 | 4/2004 | Anderson | |

FOREIGN PATENT DOCUMENTS

| | | |
|---|---|---|
| WO | WO 97/01755 | 1/1997 |
| WO | WO 99/03924 | 8/1999 |
| WO | WO 99/39204 | 8/1999 |
| WO | WO 00/00826 | 1/2000 |
| WO | WO 00/33075 | 6/2000 |
| WO | WO 02/22165 | 3/2002 |
| WO | WO 02/39120 | 5/2002 |

OTHER PUBLICATIONS de Kruif, J. et al. Rapid selection of cell subpopulation-specific human monoclonal antibodies from a synthetic phage antibody library. Proc. Natl. Acad. Sci. USA. 1995;92:3938-3942.*

U.S. Appl. No. 10/713,761, filed Nov. 13, 2003, Boyes, et al.

Wu, et al., "Targeted Proteomics of Low-Level Proteins in Human Plasma by LC/MS$^n$: Using Human Growth Hormone as a Model System", Journal of :Proteome Research, 1: 459-465, 2002.

U.S. Appl. No. 10/413,393, filed Apr. 15, 2003, Bente, H. Bryan.

Reymackers et al., "Identification of two-dimensionally separated human cerebrospinal fluid proteins by N-terminal sequencing, matrix-assisted laser desorption/ionization—mass spectrometry, nanoliquid chromatography-electrospray ionization-time of flight-mass spectrometry and tandem mass spectrometry", Electrophoresis, 2000, pp. 2266-2283, vol. 21, No. 11.

JP 2nd Office Action mailed Sep. 9, 2008—Japanese language.

JP 2nd Office Action mailed Sep. 9, 2008—English translation.

Supplementary European Search Report, Jan. 22, 2008.

Ahmed, et al., "Direct Integrin $\alpha v\beta 6$-ERK Binding: Implications for Tumour Growth", Oncogene, 21: 1370-1380, 2002.

Baygents, et al., "Recycling Electrophoretic Separations: Modeling of Isotachophoresis and Isoelectric Focusing", Journal of Chromatography A, 779: 165-183, 1997.

Berenschot, et al., "Advanced Sacrificial Poly-Si Technology for Fluidic Systems", J. Micromech. Microeng. 12: 621-624, 2002.

Bunk, et al., "Electrospray Ionization Mass Spectrometry for the Quantitation of Albumin in Human Serum", J. Am. Soc. Mass Spectrom, 8: 1247-1254, 1997.

Chen, et al., "High-Efficiency Solid-Phase Capture Using Glass Beads Bonded to Microcentrifuge Tubes: Immunoprecipitation of Proteins from Cell Extracts and Assessment of Ras Activation", Analytical Biochemistry, 302: 298-304, 2002.

A Turning Point in Proteome Analysis: Sample Prefractionation via Multicompartment Electrolyzers with Isoelectric Membranes, Electrophoresis, 21: 3639-3648, 2000.

Folkersen, et al., "Purification of Pregnancy-Associated Plasma Protein-A by a Two Step Affinity Chromatographic Procedure", Placenta, 2: 11-18, 1981.

Griffiths, et al., "Immunoadsorbent Isolation of Pregnancy-Specific $\beta_1$-Glycoprotein from Maternal Serum", Can. J. Biochem. Cell Biol. 61: 130-136, 1983.

Guzman, et al., "The Use of Selective Adsorbents in Capillary Electrophoresis-Mass Spectrometry for Analyte Preconcentration and Microreactions: A Powerful Three-Dimensional Tool for Multiple Chemical and Biological Applications", Electrophoresis, 22: 3602-3628, 2001.

Hendrickson, et al., "Improved Clean-up Method for the Enkephalins in Plasma Using Immunoaffinity Chromatography", Journal of Chromatography B, 653: 147-154, 1994.

Hendrickson, et al., "Enhanced Immunogenicity of Leucine Enkephalin Following Coupling to Anti-Immunoglobulin and Anti-CD3 Antibodies", Journal of Immunological Methods, 172: 165-172, 1994.

Herbert, et al., "A Turning Point in Proteome Analysis: Sample Prefractionation via Multicompartment Electrolyzers with Isoelectric Membranes", Electrophoresis, 21: 3639-3648, 2000.

Hiney, et al., "Gonadotropin-Releasing Hormone Neurons in the Preoptic-Hypothalamic Region of the Rat Contain Lamprey Gonadotropin-Releasing Hormone III, Mammalian Luteinizing Hormone-Releasing Hormone, or Both Peptides", PNAS, 99(4): 2386-2391, 2002.

Jensen, et al., "Identification and Removal of Polymer-and Aggregate-Forming Proteins in Human Plasma Albumin Preparations", Vox Sang, 67: 125-131, 1994.

Kubo, et al., Capillary Zone Electrophoresis of Albumin-Depleted Human Serum Using a Linear Polyacrylamide-Coated Capillary: Separation of Serum $\alpha$-and $\beta$-Globulins into Individual Components, Electrophoresis, 21: 396-402, 2000.

Lollo, et al., "Improved Two-Dimensional Gel Electrophoresis Representation of Serum Proteins by Using ProtoClear", Electrophoresis, 20: 854-859, 1999.

Mayer, et al., "Semi-Micro Solid-Phase Extraction of Organic Compounds from Aqueous and Biological Samples", Journal of Chromatography A, 773: 189-197, 1997.

Morrin, et al., "Inhibition of the Adherence of Pseudomonas aeruginosa to Epithelial Cells by IgG Subclass Antibodies", J. Med. Microbiol., 39: 459-466, 1993.

Pan, et al., "A Low-Temperature Wafer Bonding Technique Using Patternable Materials", J. Micromech. Microeng. 12: 611-615, 2002.

Panrucker, et al., "Isolation and Purification of Rat Acute-Phase $\alpha_2$-Macroglobulin", Biochimica et Biophysica Acta, 705: 174-183, 1982.

Pingali, et al., "Peptides as Affinity Surfaces for Protein Purification", Journal of Molecular Recognition, 9: 426-432, 1996.

Pitiot, et al., "Protein Adsorption on Histidyl-Aminohexyl-Sepharose 4B, II. Application to the Negative One-Step Affinity Purification of Human $\beta 2$-Microglobulin and Immunoglobulin G", Journal of Chromatography B, 758: 173-182, 2001.

Reh, et al., "Quantitative Determination of Albumin in Urine by On-Line Inununoadsorptive Cleanup and Reversed-Phase Chromatography", Analytical Biochemistry, 196: 104-110, 1991.

Ronnemaa, et al., "Relation Between Plasma Leptin Levels and Measures of Body Fat in Identical Twins Discordant for Obesity", Ann. Intern. Med. 126: 26-31, 1997.

Sand, et al., "Characterization of Human Pregnancy Zone-Protein", The Journal of Biological Chemistry, 260(29): 15723-15735, 1985.

Schneider, et al., "A One-Step Purification of Membrane Proteins Using a High Efficiency Immunomatrix", The Journal of Biological Chemistry, 257(18): 10766-10769, 1982.

Schreiber, et al., "Removal of Viral Contaminants by Monoclonal Antibody Purification of Plasma Proteins", Curr. Stud Hematol Blood Transfus. Basel, Karger, 56: 146-153, 1989.

Shimazaki, et al., "Removal of Specific Protein Spots on the Patterns of Non-Denaturing Two-Dimensional Electrophoresis Using Protein A Agarose and Antibodies", J. Biochem. Biophys. Methods, 37: 1-4, 1998.

Sorensen, et al., "Identification of a Macromolecular Crystal Growth Inhibitor in Human Urine as Osteopontin", Urol. Research, 23: 327-334, 1995.

Wheatley, et al., "Multiple Ligand Applications in High-Performance Immunoaffinity Chromatography", Journal of Chromatography, 603: 273-278, 1992.

Zhixin, et al., "Purification of Human Serum Albumin by Dye-Ligand Affinity Chromatography", Dyes and Pigments, 22: 27-45, 1993.

U.S. Appl. No. 09/660,242, filed Sep. 12, 2000, Myers, et al.

* cited by examiner

Immunoaffinity Subtraction of Plasma Proteins from a Cerebrospinal Fluid Sample

Immunoaffinity Subtraction of
Albumin and α-Acid Glycoprotein from Human Urine
Figure 7
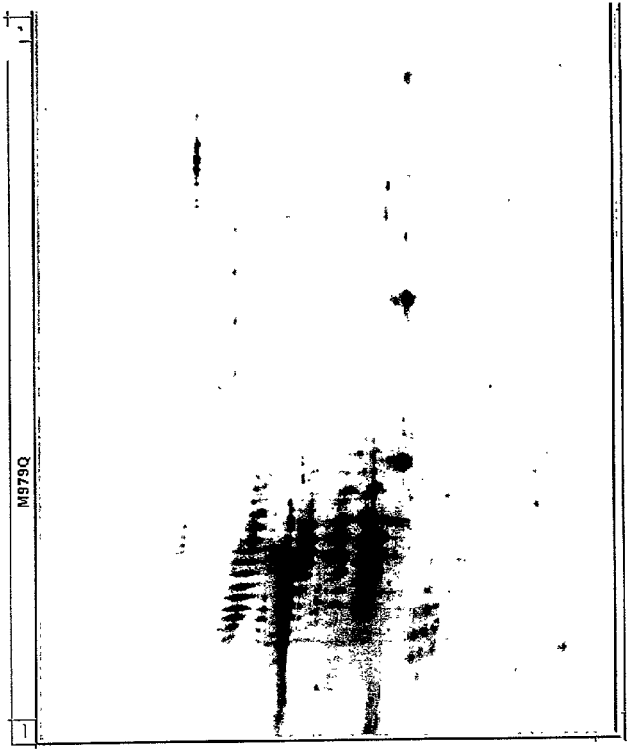
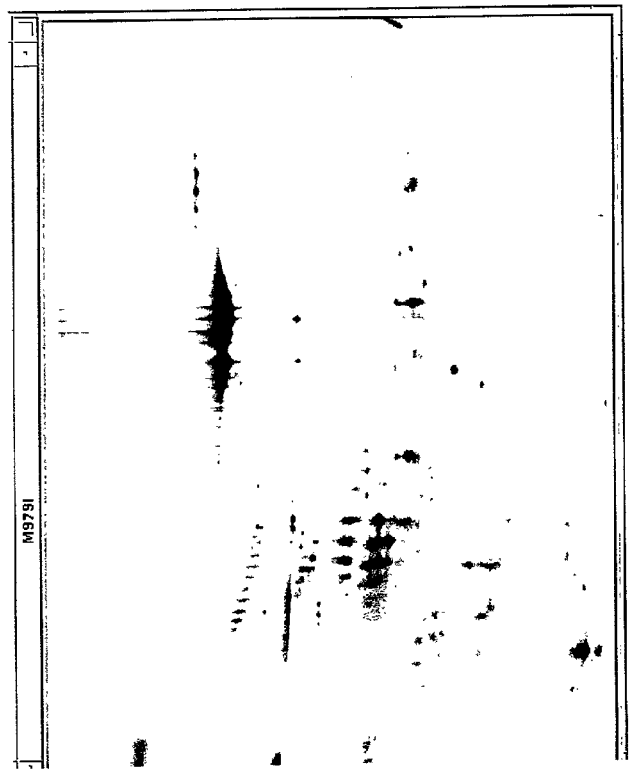

IMMUNOSUBTRACTION METHOD

This application is a continuation in part of U.S. Ser. No. 60/260,217 filed Jan. 9, 2001, the contents of which are incorporated by reference.

BACKGROUND OF THE INVENTION

A chromatographic procedure of high interest for the rapid and specific purification of proteins from complex samples is immunoaffinity chromatography. For example, see the chapter in "Methods in Molecular Biology: Affinity Chromatgraphy, Volume 147, Anuradha Subramanian, p. 95ff.; Pfeiffer et al., J. Immunol. Methods 97, p. 1-9; and Cuatrecasas, J. Biol. Chem. 245, p. 3059ff. The methodology has been refined with respect to the application of polyclonal and monoclonal antibodies for separating components from samples over immunoaffinity chromatography columns. A significant improvement for site-specific immobilization of antibodies on chromatographic matrices that facilitate binding in the first step and eluting in the second step of antigens with higher capacity was reported by Gersten & Marchalonis, J. Immunol. Methods 127, p. 215ff. and Schneider et al., J. Biol. Chem. 257, p. 10766ff.

In most cases, immunoaffinity chromatography has been used for the purification of a specific protein. In fewer cases, subtraction or removal of undesired proteins has been the purpose for the use of immunoaffinity chromatography matrices, e.g. in the specific removal of viral (protein) components from a tissue or body fluid sample (Schreiber et al., Curr. Stud. Hematol. Blood Transfus. (1989) 56, 146ff.) or in the removal of clinically undesirable proteins from blood of patients (Vallar et al., J. Chromatogr. Biomed. Appl. (1995) 664, 97ff.). In this situation, recovery of a protein mixture that has no affinity for the immunoaffinity chromatography matrix is of primary interest. Flurer and Novotny (Anal. Chem. (1993) 15, 817ff.) describe an analytical-scale procedure in which immunoaffinity chromatography columns are used to subtract proteins from human plasma to generate a plasma protein profile by second-dimension RP-HPLC.

Two-dimensional gel electrophoresis (2-DGE) is a method that enables distinguishing individual proteins in a sample that contains a plurality of proteins. Such samples include cell lysates, tissue lysates, serum samples etc. Difficulties in discriminating proteins can arise when proteins have similar charge and molecular weight so that the two or more proteins comigrate and are located in the same general vicinity of the display.

Another factor contributing to poor discrimination is the disparate abundance of one or several high abundance proteins that generally comigrate on 2-D gels with other comigrating proteins of lower abundance. In an attempt to detect lower abundance proteins, sufficient protein is loaded onto the gels such that the images on the 2-D gels are stained or labeled very heavily due to high abundance proteins thereby obliterating weaker signals of nearby, unrelated proteins. This effect may be partially ameliorated by taking a series of optical measurements as the staining develops as demonstrated in WO 01/16884.

Additionally, a limited amount of sample protein may be used in the isoelectric focusing procedure to achieve acceptable separation. 2-D gels have limits on the amount of total protein they can hold and thus it is desirable to maximize the amount of protein sample of low abundance in the gel. Thus partitioning the sample before running one or more 2-DGE has been proposed in WO 00/33075.

Such confounding conditions might be overcome by using differential detection methods that might reveal the different proteins that are situated in the same vicinity on a gel. For example, a specific detection means can be employed such as using a reagent (e.g. antibodies, receptors or ligands as reporter molecules) that specifically bind to a particular protein, and perhaps minor variants thereof. Thus, there is a need for techniques, which permit measurement of lower abundance proteins in samples containing higher abundance proteins.

SUMMARY OF THE INVENTION

It is an purpose of the invention to provide a method and means for selectively removing desired, undesired and/or abundant proteins from a sample that is to be used for protein analysis such as chromatography, electrophoresis, mass spectrometry, binding reactions, etc. The proteins removed generally are abundant in the sample so that those that one selects for those less abundant. An embodiment of the present invention that is central to the desired goals is the removal of several proteins which not only allows for the enrichment of other proteins in the samples subject to analysis, but also permits reproducible quantitation of proteins, recyclibility of the subtraction matrix and high-throughput. A goal is to simultaneously quantitate many proteins in a sample by a high-resolution technique that is compatible with the immunosubtraction technique.

To date, 2-dimensional gel electrophoresis (2-DGE) is the best available methodology allowing high resolution and high-throughput for proteins. A bottleneck of 2-DGE is that only a limited amount of protein can be applied to high-resolution, highly parallel electrophoretic protein separation resulting in hundreds of purified protein spots on a gel. Using the present invention, hundreds of additional proteins can be resolved by 2-DGE and quantitated by proteomic data analysis, when the protein sample was depleted of some proteins and simultaneously substantially enriched for other less abundant proteins.

For such a method to be successful, it should not unduly dilute the remaining less abundant proteins in the sample. Thus, for example, if about 80% or greater of the more abundant proteins are perfectly removed from a sample, the effective concentration of the less abundant proteins is increased five fold with corresponding increase in protein determination sensitivity.

BRIEF DESCRIPTION OF THE DRAWINGS

FIGS. 7(1) and (2) are images of Coomassie Blue G250 stained 2-D electrophoresis gels of urine proteins before and after chromatographic immunoaffinity subtraction.

DETAILED DESCRIPTION OF THE INVENTION

Figure 1:
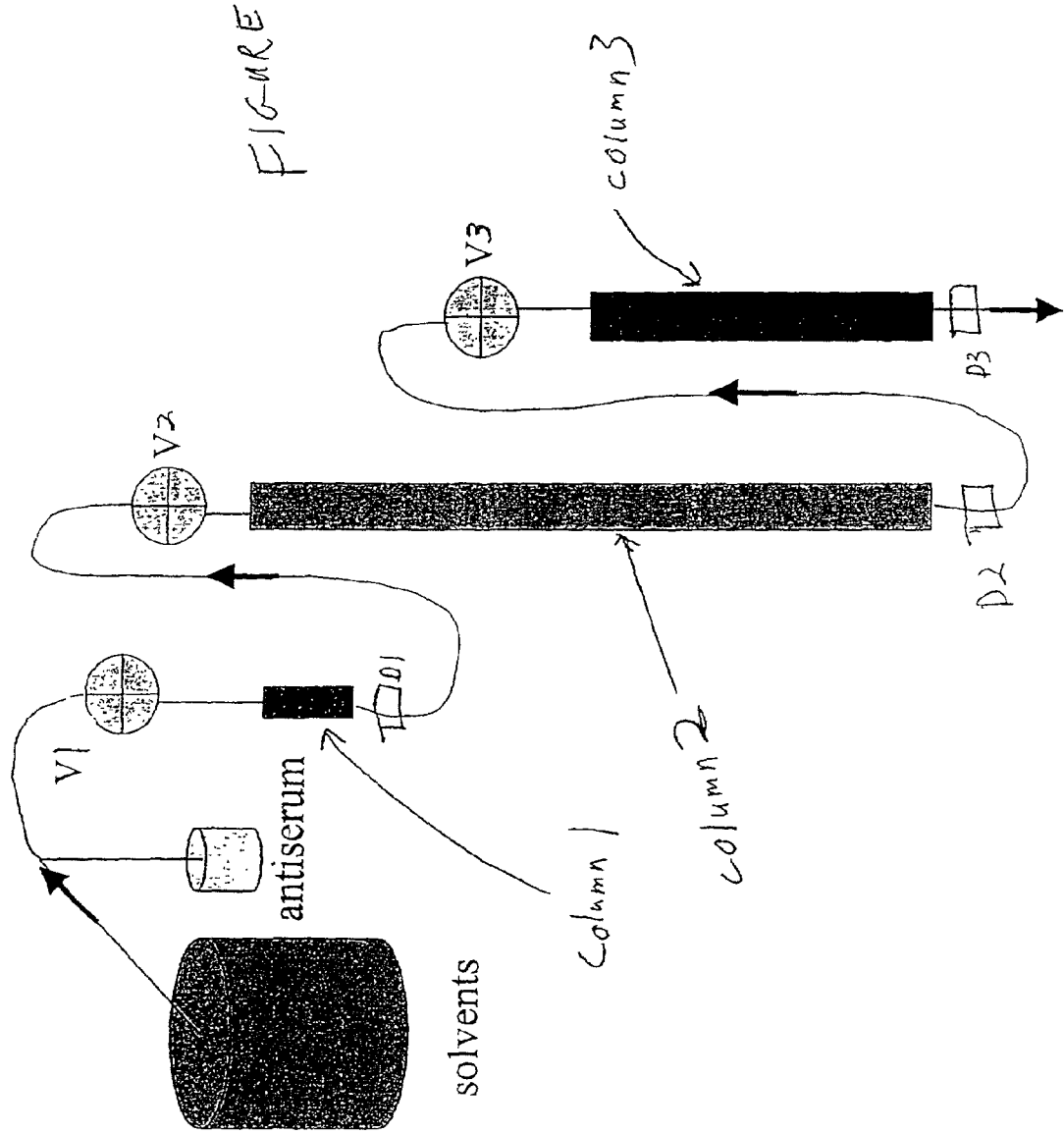
FIG. 1 depicts a system for the generation of purified polyclonal antibody from antiserum by affinity binding on an antigen column, size fraction by size exclusion chromatography and successive immobilization on Protein A.

Any sample suitable for separation and/or identification by protein separation and/or identification techniques, such as by 2-DGE is amenable to the selective partitioning of the instant invention. A particular use of the instant invention is the removal of abundant proteins from a sample to enable resolution of less abundant comigrating proteins and less abundant proteins in general on 2-D gels. The removal is facilitated by the use of low resistance matrices that speed separation and reduce dilution of the sample.

Suitable samples include cell lysates, tissue lysates, organ lysates, organism lysates, body fluid samples, subcellular fractions, environmental samples and the like. Preferably, soluble fractions of each are used. Suitable fluid samples include cytoplasm; plasma; serum; whole blood; cerebrospinal fluid (CSF); synovial fluid; tissue fluid; organ fluids, such as bile, semen and the like; humors; secretions, such as mucinous fluids, exudates, saliva and tears; waste products, such as urine and perspiration; and other biological fluids in the case of animals. For plants, microorganisms and other such organisms, various other fluids, tissue and cell extracts can be used. Thus, plant tissue, such as leaf tissue, can be macerated in a suitable buffer to yield a suitable sample. Also, a natural plant fluid, such as sap, can be used.

A variety of other environmental and biological samples contains a large percentage of one or more common proteins, contaminants, interferants, or naturally occurring high abundance substance, microorganisms or cells. Any proteometric analysis of such samples, such as by 2-DGE, liquid chromatography, mass spectrometry (including ICAT-MS), HPLC, binding assays, staining, etc., and even detection of single proteins in a sample, may benefit from the instant subtraction technique.

With environmental and industrial samples, a high abundance or interfering substance is frequently present. For example, when screening for pathogens in sewage, a very large number of relatively harmless bacteria or viruses are present. Any enrichment method, including that of the present invention, simplifies the detection and/or quantification and/or isolation of the desired material.

Removal of contaminants and interferants is important for a number of situations. Proteases and nucleases are ubiquitous in many samples and are usually unwanted as they degrade the analytes being measured. In the field of mass spectrometry of proteins and peptides, samples and intermediates are frequently contaminated with keratin because humans continually shed the protein into the environment. Such contaminated samples are not readily assayable. In such a situation, an immunosubtraction column with receptors to keratin or its peptides may be used at any time in the process from initial sample gathering to more preferable late in the process of preparation for mass spectrometry. Particularly preferred is the column's use immediately before the sample is injected into a liquid chromatography column for LC/MS.

Blood and serum proteins are also common contaminants for any tissue and thus it is preferable to remove these from such samples before finishing analysis. Also, when preparing an antigen for immunization, it is frequently desirable to remove certain immunodominant antigens or immunosuppressive compounds. Furthermore, if one wished to isolate DNA binding proteins or the "footprints" where they bind on the DNA, a selective removal system is also desirable. In conventional immunoassays, clinical chemistry and other analysis of biological liquids naturally occurring proteins frequently interfere. Samples, which contain large amounts of proteins such as albumin, are notoriously difficult to work with due to turbidity, adsorption of analytes, etc. The conventional way to solve the problems is to dilute the sample with saline. While this does work, the concentration of a low abundance analyte is reduced even further, perhaps to the undetectable range. The present invention is useful for removing the interfering materials in a biological sample without significant dilution, and indeed may even involve concentration to aid in the detection and quantification of such low abundance analytes.

Plants have a number of common proteins depending on the tissue selected. In the seeds of beans, about 40% of all protein is phaseolin. For corn seeds, common proteins include zein, globulins, protamines and glutinins. For many of the oil seeds, one or a few storage proteins comprise a large percentage of all protein.

Outside of the storage proteins of seed, leaf tissue from most plants contains about 20-30% Rubisco, considering the large and small unit thereof, with higher levels after exposure to light and lower levels in the absence of light. Other common proteins include ribosomal proteins, both chloroplast and cytosolic, thylacoit, photosynthesis system I proteins, photosynthesis system II proteins, chloroplast membrane binding proteins and other structural proteins.

Should the plant, or plant cells in culture, be infected with a virus, whether natural or man-made, large percentages of total protein may be viral, for example, 20-30% of tobacco mosaic virus coat protein may be found in total protein samples from infected tissues.

Likewise, bacteriophage infected bacteria and virus infected animal cells might contain large percentages of viral proteins in the total protein sample.

Hence, removal of interfering or abundant proteins is desirable in those circumstances as well.

The proteins to be removed from the sample are done so by exposing the sample to receptors that specifically bind the proteins to be removed. Preferably, the binding is reversible to enable reuse of the binding agents as well as recovery of the isolated protein species. Suitable binding molecules include antibodies; lectins, such as concanavalin A, wheat germ agglutinin, abrin and so on; receptors; metals; co-factors; combinatorial compounds, polymers, nucleic acids, artificial protein sequences designed to act as specific binding receptors for the ligands being removed (aptamers) and other compounds that bind particular classes of proteins, such as heparin, polymyxin, dyes, such as Cibacron blue F3GA, and hydrocarbons, such as methyl and phenyl radicals that bind hydrophobic proteins. Often the agents comprise a functional group to which a protein is attracted. Examples of such functional groups include hydrazide, amine, N-hydroxy-succinimide, carboxyl, boronate and organomercury.

While this patent application generally refers to removal of proteins from a sample, the same techniques may be used for removing any ligand such as contaminating, interfering or simply high abundance substances, complexes, particles and even whole microorganisms or cells. Likewise, while antibodies are exemplified as the specific binding partner, any receptor that specifically binds to a ligand in the sample may be use for the presently described technique. The ligand and corresponding receptor bind relatively specifically to each other. Neither ligand nor receptor need be a single compound but may also include complexes, particles and larger structures. While this patent application uses the terms affinity and immunoaffinity for the specific examples, these should be interpreted broadly to refer to specific binding relationships between the receptor and ligand.

A preferred binding molecule is an antibody. The antibody can be of any animal species. The antibody can be natural or produced recombinantly. The antibody can be of any class, subclass, single chain and monofunctional, bifunctional or polyfunctional. The antibody can be intact or substantially intact, that is various portions of the antibody can be removed so long as the desired functions, such as antigen binding or Fc receptor binding, is retained. Hence, glycosylation sites can be deleted as well as can Fc receptor binding ability.

Monoclonal antibodies are powerful reagents because a clone can yield an antibody of high affinity, high avidity or both in essentially unlimited quantity and reproducible quality. Individual antibodies can be examined as taught herein to ensure that binding of the antibody to the matrix does not compromise antigen binding. Moreover, use of a monoclonal antibody should preclude the need for antibody purification using a matrix to which is bound the cognate antigen of interest as taught herein.

The specific binding agent bound to the matrix for removing a high abundance protein from the sample may also be a recombinantly produced, single chain, diabodies or antibody display phage. When antibody display phage are used and conventional panning employed in its preparation, very high affinity and/or high avidity display phage are prepared. However, any antibody, which lacks the Protein A, or G binding Fc portion will require a different attachment mechanism. However, since display phage are inherently polyvalent they may be immobilized on a solid phase by many techniques and still have functional antibody-like moieties free for antigen binding.

Antibody fragments such as Fab or Fab2 may be used but will utilize a solid phase with a specific binding agent for the non-epitopic region of the Fab. Bifunctional antibodies (diabodies and reassortant Fab2 or reassortant antibodies) each may have a first antigen binding portion and a second antigen-binding portion. One may advantageously have the solid phase bound to the first antigen as a way for immobilizing the bifunctional antibody which may then be crosslinked as described herein. This leaves the binding site for the antigen being removed from the sample free for binding.

Recent developments with synthetic receptors appear promising. These are combinatorial peptides, oligomers, polymers, etc. either alone or used within a longer polymer sequence. For the purposes of the present invention, these are also considered receptors.

To facilitate the separation and removal process, it is preferable that the binding molecules be immobilized on a solid phase that is inert to the binding agent and to the sample. The binding agent is affixed to the solid phase using known procedures and in a fashion that does not substantially reduce the protein binding ability of the binding agent or molecule. Moreover, to facilitate reproducibility of the matrix, it is preferable that the binding molecule be stably bound to the solid phase. Thus, for example, the binding molecule can be adsorbed, bound covalently to or entrapped in the solid phase, attached to or incorporated into a coating for the solid phase.

Preferred solid phase for immobilizing binding agents or molecules are matrices that have enhanced surface area. A suitable matrix is, for example, a bead or a microbead shape and form. Such beads or microbeads generally are spheres of a particular resin or polymer having properties suitable for such affinity chromatography, such as binds antibody, substantially inert to the antibody, substantially inert to the sample, is stable under conditions used for the separation process and so on.

Suitable matrices are beads made of materials such as dextrans, styrenes, agarose, calcium phosphates, acrylics, polyamines, acrylamides or silicas. Collectively, these may be referred to as "resins" in this application even though materials such as silica are not usually chemically considered "resins". Many such materials are available commercially, for example, from Pharmacia, Bio-Rad, Sigma and other distributors. Preferred matrices are those that permit high flow rates with low back pressure. Particularly preferred are high throughput techniques using protein porous matrixes, such as porous beads that enable perfusion chromatography, such as POROS™ (a trademark of Applied Biosystems, Foster City, Calif.) chromatography media; and continuous bed matrices such as UNO™ (a trademark of Bio-Rad Laboratories, Richmond, Calif.) chromatography columns. Other suitable matrixes are produced by Pharmacia and others.

For fast separation, it is preferable to use a solid matrix, which will allow liquids to rapidly pass through or by the matrix. When one wishes to treat a considerable number of samples identically by sequentially passing them through the same matrix after elution of previously bound material, the rate at which the sample passes through the matrix becomes a time-limiting factor. "Perfusion" matrixes are particularly preferred for this technique but other matrixes may be used also. In some of the examples below, over one hundred were passed through the same column with time to complete one cycle of sample loading, unbound protein elution, adding elution buffer, bound protein elution and final wash being approximately 15 minutes or less.

Because the samples destined for separation are generally of low volume, it is desirable to have a separation process that is quick and does not unduly dilute the sample, particularly since the void volume or that portion of input proteins that do not bind to the solid phase matrix, will contain those proteins that are not abundant in the original sample.

POROS particles represent microspheres of styrene and divinylbenzene that are interadhered to create essentially circular particles with an abundance of pores and channels within the interior of the particles. The result is a highly porous particle wherein effective binding occurs not only on the surface of the particle but in the interior as well. Thus, high flow rates can be used.

UNO columns contain continuous bed matrices that contain a homogeneous matrix rather that discrete structures, such as beads. Thus, monomers and ionomers are polymerized in situ. The polymer chains aggregate into a dense network of nodules consisting of microparticles. The result is a column that can tolerate high flow rates without sacrificing resolution and capacity.

Other preferred solid phase matrices can be used so long as the flow rates usable with the other matrices are comparable to or faster than that used with the POROS and UNO matrices.

Thus, either the matrix itself binds or entraps a particular protein or class of protein, is derivatized or modified to carry out that function or entraps a molecule that can carry out that function. For example, a particular binding agent is affixed to a surface of the matrix. By way of example, a binding molecule, such as an antibody specific for a particular sample protein, is affixed to the matrix. The antibody, or other receptor(s), can be monoclonal or polyclonal, that is they recognize one or plural epitopes on the ligand to be removed. Polyclonal antibodies are useful because the polyclonal preparation binds to different epitopes and determinants of the protein to be removed rather than being restricted to a particular determinant. Binding of a particular antibody to the matrix could have an untoward effect on the antigen binding ability and capacity of any one antibody species. Thus, a polyclonal antibody offers certain advantages.

One way to affix antibody to the matrix is by the use of protein A and/or protein G and/or protein L or the like that are known to bind to the FC portion of immunoglobulin. Protein A and protein G have particular affinity for different classes and subclasses of antibody as well as for antibodies obtained from different animal species. Either the affinity of any one antibody preparation for protein A or protein G is known or can be determined practicing the methods taught herein.

Matrices carrying protein A or protein G covalently bound to the surface thereof are available commercially, for example, from Applied Biosystems and Bio-Rad. Alternatively, matrices carrying hydrazine groups that bind to the FC portion of immunoglobulin by way of covalent hydrazone bonds can be used in similar fashion. Other methods to immobilize antibodies onto the solid phase may be use but are generally less preferred because of difficulties controlling the binding reaction or because they result in more antibody becoming inactive resulting in lower binding capacity.

Thus, the antibody preparation is mixed with the matrix under conditions suitable for facilitating binding of antibody to the matrix. Once bound, it is preferable to bind the antibody to the matrix covalently to provide a matrix that is stable to treatment without substantial loss of antibody. Methods for covalently binding antibody to protein A, protein G or to the matrix are known. For example, bifunctional crosslinking molecules are well known for this purpose, such as glutaraldehyde, dimthyladipinidate, dimethyl suberimidate (DMS), dimethyl pimelimidate (IMP), tetranitromethane and dimethyl 3,3' dithiobisproprionimidate that generate imidamide crosslinking and such conjugating bonds are known in the art. While any may be used, it is preferred to use plural crosslinking agents to tightly bind the receptor to the matrix or matrix having an intermediate binding agent such as Protein A or G as each crosslinking is preferred for slightly different spacing between reactive moieties.

To ensure the antibody is specific for the protein to be removed, the antibody preparation can be purified to remove cross-reacting antibody, particularly if polyclonal antisera is used. To refine the specificity of the antibody, the antibody preparation can be fractionated by exposing the antibody to the particular cognate antigen protein. The particular cognate antigen protein can be bound to an inert matrix as described hereinabove to yield an affinity chromatography matrix for isolating antibody that specifically binds to that protein. It is preferable that the protein affixed to the matrix be of high purity to enhance the specificity of the antibody preparation. The matrix used is one amenable to binding proteins and generally would not be one to which protein A and protein G are affixed as the matrix or derivatized form thereof must be specific for the antigen binding site and be bound by the antigen binding site of the antibody preparation to be purified.

Thus, the antibody preparation may be exposed to the corresponding matrix containing the protein of interest, that is, the protein which is to be removed from the samples for further analysis, in a batch, column or other suitable format and incubated so that the antibody is retained on the matrix, eluted and collected for use as provided herein.

For the consistent manufacture of binding matrix, a reproducible process that is readily automatable is preferred. This involves two important features, 1) preparing a means for purifying the receptor using the ligand and 2) using the receptor to remove ligand from the sample. For example, an affinity matrix can be used for purifying receptors. First, purified ligand is mixed with the preactivated matrix material to bind the ligand. Alternatively, the ligand may be chemically bound to the resin as a separate step. Alternatively, the ligand may be derivitized so that it will bind to the matrix directly (e.g. biotinylated ligand and avidin bound matrix) or easily reacted with the matrix. The ligand matrix then is loaded into a column or similar format using a known buffer to form a first column. Reactive groups of the preactivated matrix bind, preferably covalently bind, to complementary groups on the ligand. Generally, saturating amounts of ligand are added to the matrix. The matrix is washed resulting in ligand covalently affixed to the matrix. Optionally, a blocking agent may be added to reduce non-specific absorption of receptor to the matrix. The ligand matrix can be used in batch format and/or can be packed into a column. The receptor preparation is then added to the matrix and incubated under conditions to enable specific binding. The bound receptor is eluted from the matrix, for example, by exposure to a low pH. The eluate is monitored for ligand, for example by UV 280 absorption with protein ligands and the protein receptors collected.

Similar formats to columns include mixing of matrix in a liquid sample whether the matrix is loose beads or in permeable packets, magnetic matrix beads, microarray formats where different receptors are immobilized on different locations on the matrix(es), liposome or micelle emulsions, dipsticks, tube coatings, etc. The key feature is that the matrix is partitionable from the sample liquid.

The first column then can be connected in series to a second column, which removes elution agent(s), for example, a size exclusion column, such as one containing Sephadex, optionally with a neutralizer of buffer. The purified receptor from the first column passes through the matrix and is excluded therefrom which effects salt removal, which is not so excluded. Again, the eluate can be monitored for protein, such as by 280 nm absorption when protein ligands and/or receptors are used.

The second column then is connected in series to a third column, which would be packed with a preferred matrix containing a moiety reactive for binding the antibody.

To begin the process, a receptor preparation is added to the first column and allowed to pass through the column. Receptor specific to the ligand attached to the ligand matrix will be retained on the column and unbound substances are discarded. Following such binding, the receptor is eluted from the ligand matrix, for example, by exposure to an acidic or alkaline buffer, a chaotropic or denaturing agent (preferably reversible). The eluted receptor in the acidic buffer then is optionally neutralized, channeled to the second size exclusion column to effect salt exchange. The eluted receptor then is optionally neutralized if not already done and channeled to the third column containing the matrix for binding receptor. The third column is loaded with receptor until the desired binding capacity of the column for receptor is obtained. The result is a column containing a matrix containing an antibody specific for a particular protein.

The matrix bound to receptor then is optionally treated using known methods to permanently bind, e.g. covalent attach the receptor thereby "fixing" the receptor to the matrix. The result is a matrix suitable for repeated use in removing the cognate ligand from a sample. The binding capacity of a unit volume or weight of matrix for the cognate ligand is determined using known methods.

The collected receptor can be tested for specificity to the ligand of interest using known methodologies, such as a separate binding assay.

Then the receptor is then bound to a matrix as taught herein to yield a reagent for removing the cognate ligand from a sample destined for later analysis or purification and/or detection of analytes in the sample, such as by 2-DGE.

In lieu of initially immobilizing the ligand to a solid phase, free ligand may be used and mixed with receptor. If the receptor is at least divalent, an insoluble complex may form which is readily recovered separate from the remainder of the liquids being used. Separation may be by filtration, decanting, centrifugation, etc.

Alternatively, if the ligand is labeled with a binding partner, such as biotin, a complementary binding partner, such as avidin, may be bound to a solid phase before or after contact with the receptor. In this matter, receptor-ligand complexes may be removed from solution by binding to the solid phase. Free receptor is then eluted therefrom. Other formats for using the ligand to purify the receptor may also be used.

Thus, for example, suitable antibody specific for a particular protein that is to be removed from a sample can be attached to a preferred matrix to provide a reagent of interest. The process of obtaining a specific antibody preparation, purification of that specific antibody and binding of the antibody to a preferred matrix can be accomplished in a series of columns. The process is repeated for other proteins to yield a number of matrix reagents specific for the particular proteins to be removed from a sample.

Removal of glycoproteins can be beneficial as many proteins carry graded amounts of carbohydrate yielding plural molecules of similar charge but different molecular weight. Such molecules yield a horizontal array of spots in a "train" on the 2-D gel. Because such trains can add complexity to the 2-D display and can confound resolution and discrimination, removal of glycoproteins can be beneficial. Moreover, methods to remove glycoproteins will enable comparisons of samples that are and are not glycosylated. It is known that oncogenesis often is accompanied by disruptions of normal glycosylation of cells.

When separation based on glycosylation is important, lectins can be affixed to a matrix as taught hereinabove to provide a matrix that will bind molecules carrying the particular sugar or sugars to which the lectin binds.

An alternative method to remove trains is to expose the sample to a saccharidase or glycosidase to remove carbohydrate bound to proteins in the sample. A number of carbohydrates are known to be bound to proteins and any of a variety of enzymes that cleave a particular sugar can be used.

For example, many glycoproteins are sialylated, once or multiply. Thus, the sample can be treated with a neuraminidase to remove the one or more sialic acid residues from the protein. Many glycoproteins are fucosylated. Hence, one or more fucosidases can be used to remove fucose residues. Because carbohydrates can be linked to proteins and to other sugars in a variety of linkages, such as, 1→3 or 1→4, and some enzymes are specific and cleave only a particular linkage, a robust enzyme or several enzymes may be employed to remove sugar residues. The samples are treated with the suitable saccharidase(s) or glycosidase(s) under the appropriate conditions to obtain the desired deglycosylation.

Unlike the above procedure using a binding agent such as an antibody, which generally binds to only a particular molecule, a deglycosylation likely would remove a number of proteins, or a class or proteins, as compared to a particular protein. When analysis of different glycosylation is desirable, the use of a lectin column is preferable.

A separate purpose of the instant invention is to provide reagents that can be combined, for removing multiple selected proteins from a sample. Generally, plural proteins are removed from the sample. Thus, a multifunctional matrix that binds a class of proteins or a plurality of individual matrices carrying different agents, such as antibodies of different specificities, are combined. When plural specific matrices are used, the different specific matrices can be mixed in a batch. The mixture can be maintained and used in a batch format or can be loaded into a column. In that case, the different species of matrices can be mixed together.

Alternatively, when a column format is used, different matrices carrying different binding agents can be mixed before adding or loaded sequentially, wherein the individual matrices may be separated by an inert carrier, such as a porous membrane, in layers, or the individual matrices can be contained in a separate column. In such a situation, at least one receptor is a division of receptor(s) that is at a separate predetermined location from at least one other division of receptor(s).

When individual matrices specific for binding different proteins are to be mixed, it must be ascertained that the combination does not substantially lessen the binding capacity of any one matrix for the cognate protein. That exercise can be conducted using standard techniques of establishing the binding capacity of any one matrix alone and comparing the binding capacity of that cognate protein in a mixture.

It thus is possible to produce certain combinations of particular matrices in a mixture that is particularized for certain samples. Hence, a particular combination of specific matrices can be used reproducibly for serum samples because it is known what are the more abundant proteins in serum. In the same fashion, a particular mixture can be configured that would remove the more abundant proteins from plasma, urine, CSF and other biological samples.

Thus, in another format, individual matrices carrying different binding agents are housed in separate vessels, layers or compartments therein, and/or the vessels are connected sequentially in series, connected, for example by a conduit or tubing.

Different receptor matrixes are stable for different periods of time. Some receptor matrixes prepared by the methods of the Examples below have been stable for hundreds of cycles of use, stripping and reequilibration without loss of specificity or effectiveness. Other matrixes have been stable through only a dozen or two cycles before showing signs of degrading. The factors determining stability include receptor choice, matrix choice and immobilization technique.

Where some of the receptors or ligands are subject to degradation before others, it may be desirable to have matrixes bound to the labile receptors or ligands to be present in a separate column for easy removal and replacement with fresh binding receptor to avoid replacing the entire column. Alternatively, labile binding partners may be located inside a separate layer separated by permeable membranes or inside a permeable bag or packet and placed inside the column such that they may be easily separated for replacement. A permanent subcolumn section or chamber, such as a thick metal ring with a fine mesh on top and bottom, enclosing the labile binding partner matrix may be used. This structure has been used for different purposes previously such as in U.S. Pat. No. 4,636,361. For particulate matrixes, those bound to labile binding partners may have magnetic, paramagnetic or diamagnetic materials incorporated therein. Those matrix particles may be readily separated by removing all matrix particles from the column and applying a magnetic field or other magnetically responsive member. The key feature to all of these designs is to have the labile matrix-receptor be selectively removable from the stable matrix-receptor for easy replacement.

The choice of which matrices are to be combined into a mixture may not be arbitrary and may be facilitated by observing that certain proteins to be removed that may share a common property. One suitable property is elution from the matrix following the removal procedure. Thus, proteins that can be eluted from the antibody-containing matrices using a single buffer can indicate which matrices can be combined. If different loading or elution conditions are preferred, different columns are preferred for those antibodies preferring different conditions, creating at least the same number of columns as elution conditions.

The retained proteins can be of use. For example, if immunoglobulins are removed from the sample, the recovered immunoglobulin may be used for treatment or the subject of diagnostic assays, for example, to determine whether the removed antibodies bind to a particular antigen. The quantity of certain removed proteins is also indicative of certain conditions. For example, abnormally low levels of albumin are found during certain liver diseases, tissue damage and starvation. Likewise transferrin abundances is affected by amount of iron, liver and kidney diseases. Also, alpha antitrypsin is increased during pregnancy and has even been used as a marker for inflammation.

The use of separate matrices for separate receptors is preferred because different receptors will compete or interfere with each other's binding. With a less controlled reaction, determining the binding capacity of the matrix for each ligand becomes less predictable. Furthermore, as an industrial process, binding many different receptors to a single matrix simultaneously is difficult to control.

When plural matrices are combined into a mixture, preferably the binding capacity of any one matrix is determined and the relative amount thereof in comparison to the binding capacity of other matrix types is adjusted to ensure uniform usage over time. The relative binding capacities can track the relative abundance of the proteins in the sample. Thus, in the case of one particular protein, it can be determined that one milligram of matrix containing an antibody specific for albumin, for example, binds 2 mg of albumin. That can be determined by exposing a known volume of matrix to graded amounts of a protein solution of known concentration. Then it can be determined, for example, by monitoring the 280 nm absorbance of the fluid following exposure to the matrix, when the matrix has bound as much albumin as practical. The binding capacity of the matrix as well as the efficiency of removing bound protein can be assessed by monitoring protein levels in the sample and in the eluate, using standard methods such as, ELISA, 280 nm absorbance or protein dyes.

It is known that generally, serum contains about 44 mg/ml of albumin. Thus, to remove essentially all of the albumin in a 50 µl sample of albumin, it will be necessary to expose the serum sample to at least 1.6 mg of matrix.

Also, suppose proteins A and B each comprise 30% of the total protein in a sample. Protein C comprises 20% of the total protein in the sample. Three matrices that each specifically binds A, B or C are prepared. Assume each matrix binds the same molar amount of A, B or C and A, B and C can be eluted from the respective specific matrix using the same buffer. To remove A, B and C from the sample, matrices A, B and C can be mixed at the ratio of 37.5:37.5:25, either in a batch or sequentially in a column(s) to yield a reagent that can subtract A, B and C from such a sample. The sample is applied to the reagent and allowed to incubate with the reagent to enable A, B and C to bind to the respective matrix. The eluate sans A, B and C is collected.

Any of a variety of available assays can be used on the eluted sample to ensure removal of the protein(s) of interest. For example, an ELISA can be performed on the eluted sample to determine if capacity of the binding ability of any one matrix is exceeded by presence of the protein sought to be removed in the samples. If present in the eluate, it may be desirable to recycle the sample over regenerated matrix or over fresh matrix.

The final eluate is collected and then treated to concentrate the proteins remaining in the sample and to ensure that the proteins are in a buffer suitable for 2-DGE or other use for measuring the proteins. The sample can also be dialyzed, lyophilized and so on.

An optional deglycosylation step can be conducted on the separated sample, particularly if the separation did not include a reagent for removing glycoproteins. For example, the sample can be incubated under suitable conditions with a neuraminidase, such as, sialidase A distributed by Prozyme, which is a recombinant enzyme with broad substrate specificity.

Following enzymatic treatment, the sample is preferably desalted, optionally separated from the enzyme and made ready for isoelectric focusing. The succeeding steps are known in the 2-DGE art per se.

In any one sample source, the goal is to remove the most abundant proteins so that the effective concentration of the less abundant proteins is enhanced. Various protein separation and detection may be used before or more preferably after the subtraction technique of the present invention.

In the case of animal serum samples and particularly human serum samples, some of the more abundant proteins are immunoglobulins, albumin, transferrin, haptoglobin, $\alpha$-1-antitrypsin, hemopexin, $\alpha_1$-acid glycoprotein, myosin, transthyretin, $\alpha_1$-antichymotrypsin, apolipoprotein AO, $\alpha_2$-macroglobulin, fibrinogen and prealbumin. A similar profile exists for cerebral spinal fluid. For urine samples, albumin and alpha acid glycoprotein are the most abundant proteins. For tissue samples, contamination by blood and serum proteins is common and thus albumin, hemoglobin and any other serum protein mentioned above are contaminants for removal. Thus, several proteins can be removed. That would represent subtraction of at least about 85% of the total proteins. However, the number of proteins that can be removed is not limited as different matrices can be made to bind to the individual proteins and used to subtract those proteins from a sample. Thus, 2, 3, 4, 5, 10, 15, 20, 25, 30, 35, 40, 45, 50 or any number in between and even more proteins can be removed to yield samples that can be concentrated to contain discernible amounts of proteins that generally cannot be resolved.

In other samples, perhaps only a few highly abundant or highly interfering proteins may desirably be removed. Put in another way, it is desirable to remove at least 40% of the protein of a sample in the practice of the instant invention. Preferably, at least 50% of the proteins can be removed. By increasing the number of particular matrices used, more than 50%, more than 60%, more than 70%, 75% or more, more than 80% and even more than 90% of the proteins found in a sample can be removed prior to further analysis. In one example below, the original serum protein concentration was 88 mg/ml. After passage through the column, 74 mg/ml was removed and the flow-through effluent, after concentration, contained only 1.4 mg/100 microliter aliquot. Theoretically, the amount of removal is limited only by the abundance of various ligands in the samples and the number of corresponding receptors used to remove them. Representative percentages can be seen from Table 1 above, which will differ with different sample sources. A list of most common proteins or interfering proteins for other samples may likewise be determined (if not already listed in the public literature) and from these one can choose appropriate antibodies to use.

The particular proteins to be removed from any one sample are discretionary based on the abundant proteins found in the sample. Different samples can have nearly the same or different abundant proteins that are to be removed. In plant samples, ribulose biphosphate oxygenase/carboxylase (Rubisco) is generally one of the more abundant proteins in many plant leaves.

For a sample where it is unknown which proteins are abundant proteins, one may first do a preliminary separation and analysis to determine the most abundant proteins. Antibodies to these proteins are then generated and used to remove the abundant proteins. The process may be repeated to obtain the desired removal.

The use of such reusable matrices for removing abundant proteins enables the identification and resolution of less abundant proteins in a sample in a reproducible and high throughput fashion. Reproducibility enables comparisons between and among samples. It is preferable to run every sample in a batch or experiment through the same column(s) to control for any variation in immunosubtraction.

Many of the methods and reagents of the instant invention are amenable to automation, further enhancing throughput and reproducibility. The separation technology currently available can be automated, such as commercially available chromatography columns and stations, such as the INTEGRAL and BIOVISION workstations distributed by Applied Biosystems. Such workstations enable setting up a plurality of columns in series wherein the various columns can be eluted with different buffers. Moreover, in the case of 2-DGE, many of those procedures also are amenable to or are automated. For example, see applicant's previous patent, Anderson et al, U.S. Pat. No. 5,993,627. The result is a highly reproducible system that yields results in a very timely fashion.

By "abundant" is meant those proteins that are more plentiful in a sample, based on, for example, actual relative amounts of the various proteins in the sample. Abundance also can be revealed as a protein spot that stains quickly and heavily on a 2-D gel. A measure of abundance is to ascertain a relative measure, for example, as compared to the total amount of protein. A densitometric scan of a stained gel can provide such a measure. A 2-D gel containing separated, stained proteins is obtained and scanned in a densitometer. The densitometer then will calculate the total amount of stained proteins on the gel and the relative percentage of any one protein relative to the total. Using such a calculation, an abundant protein is one that represents at least 1% of the total protein in a sample.

"Protein" as used herein is any polymer comprising amino acids irrespective of function. The protein may be altered by having other chemical moieties contained therein such as phosphates, sugars and other organic groups. Thus, a dipeptide containing two amino acids, wherein the dipeptide has no known function, is for the purposes of the instant application, a protein. Another term for protein is polypeptide. The protein can be obtained from an animal source, a microbial source, and environmental source or a plant source.

The invention now having been described thoroughly, various aspects of the invention are provided in the non-limiting Examples hereinbelow.

Demonstrating the Capabilities of the Technology

The present invention describes a procedure that combines a novel high-throughput immunoaffinity chromatography-based technology and successive quantitative protein sample analysis by 2-dimensional electrophoresis of samples that had been subjected to multi-component immunoaffinity chromatographic protein subtraction. While individual aspects of the described immunoaffinity chromatography methodology and its application in combination with 2-dimensional electrophoresis have been reported, no application is known and published, that (i) describes individual immunoaffinity matrix generation methods in simple two-step chromatographic procedures, that (ii) generates separate chromatographic matrix materials for each immunoaffinity component which may be used in any proportion desired, that (iii) succeeds in the generation of reproducible multi-component "pooled" chromatographic matrices, that (iiii) demonstrates the extensive recyclability (>300-fold) of multi-component chromatographic matrices, that (iiiii) is a high-throughput automated procedure (throughput of >50 samples a day), and that (iiiiii) allows accurate quantitation of pure proteins after the chromatographic sample has undergone 2-dimensional electrophoretic separation. Furthermore, to succeed in obtaining high-throughput, a chromatographic matrix was chosen to allow high flow rates, efficient binding, and fast regeneration of the matrix. Perfusion chromatography is ideal for high sample throughput made possible by the high surface-to-volume ratio of highly porous beads. A manufacturer of such perfusion chromatography matrices ("POROS" beads) is Applied Biosystems Inc., (Framingham, Mass.).

The technology described here is applied to, biological samples such as, but not restricted to, fluid samples from organisms or fluids derived from parts or the whole organism. It is particularly applicable for analysis of proteins in these samples, because it allows the quantitation of at least 50% more proteins from the fluids without substantially loosing sample throughput. In addition, there is flexibility to convert the chromatographic separation procedure using immunoaffinity with another affinity or other chromatography procedure, suitable for a specific type of sample that generates two or more fractions for each sample. A method for serum protein fractionation was exemplified that combines the immunoaffinity with wheat germ agglutinin (lectin) affinity chromatography.

PREPARATIVE EXAMPLE A

Generation of Individual Chromatographic Immunoaffinity Matrices

Unlike previously published methods for immunoaffinity chromatography, the following described techniques yield very high purity of antibodies and very high specificity of the immunoaffinity chromatographic matrices containing them.

Affinity chromatography matrices were generated using a POROS matrix that is used for perfusion chromatography; derivatives of this matrix were acquired from Applied Biosystems. Size exclusion chromatography columns (SEC) were from Bio-Rad. Antisera were acquired from many different companies and the titers determined to select antisera with the highest concentrations of active pure antibody. POROS-AL is a pre-activated (aldehyde-function) matrix that was used to immobilize proteins covalently. For all proteins to be removed from a given body fluid sample, a protein affinity matrix was generated as the "selecting" reagent for pure specific antibodies from complex antisera. The reagents were (a) pure protein either commercially available or additionally purified and (b) the POROS-AL matrix. The protein affinity matrix was generated in a batch procedure. Thus, as many individual protein-derivatized affinity matrices were synthesized as there were proteins to be subtracted from a given sample.

POROS-G 20 and POROS-A 20 are matrices that are already immobilized with a specific protein. The proteins are protein G and protein A, respectively. These two proteins have an extremely high affinity for Fc fragments of antibodies and are thus ideally suited to immobilize antibodies in a site-oriented manner. The considerable advantages of protein A and protein G readily coupled to a matrix are (a) the stabilization of antibodies in an immobilized state, (b) the correct orientation of antibodies with all Fab fragments available for interaction with the corresponding antigen and (c) a very efficient covalent coupling step that does not interfere with the structure of the antibody molecule.

FIG. 1 depicts a chromatographic system and process used for purifying antibodies from antisera and immobilizing them on an affinity column. The system used column switching valves, V1, V2 and V3 for multiple columns. Column one is an antigenic protein column (packed from the abovementioned activated POROS-AL matrix. Column two is a SEC column that neutralizes the acetic acid-eluted antibodies, partially removes salts and sieves the molecules through the pores before affinity-trapping them on the POROS A or G column. A series of the antiserum-loading and antibody-trapping one-step chromatographies were carried out until the POROS A or G column was saturated with antibody. The saturation process can be monitored by measuring absorbance at UV280 directly through the detectors D1, D2 and D3 of the chromatography station.

Once an antibody column is obtained, the immobilized antibody is crosslinked to the protein A or G and thus covalently attached to the matrix using 50% dimethyl pimidimylate (DMP) and 50% dimethyl suberimidate (DMS) as the bifunctional crosslinker following conventional procedures for 100% DMP crosslinking. DMP/DMS works effectively in an "on-column-crosslinking" procedure due to its rapid reaction with amine groups and the coupling of protein A or G and the antibody via iminoamide bonds. Under acidic and neutral pH conditions, the chemical bonds are very stable and allow recyclable use of the antibody column for protein antigen binding and elution.

PREPARATIVE EXAMPLE B

Pooling of Matrices to Multi-Component Chromatographic Systems

The above-described procedure can be exercised for numerous protein antigens and thus numerous immunospecific antibody-derivatized matrices can be generated. The presently described invention has flexibility of use of such antibody-derivatized immunoaffinity chromatography matrices. Individual matrices are generated and defined volumes or weights can be packed into columns.

The column capacity for antigen binding can be evaluated by individually loading antigen stepwise onto the column until a saturation peak is observed. Thus, the maximal amount of the antigen that can be trapped on the column can be calculated individually for every antibody-derivatized matrix. Pooling the matrices into multi-component immunoaffinity systems with defined capacities for multiple protein binding allows one to generate a specific chromatographic column for a specific purpose. The following table is an example how such entities are useful. Serum contains a few very abundant proteins. In order to be able to detect lower abundance proteins in a "downstream" procedure such as 2-DGE, it is of interest to subtract the abundant ones. With the above-described multi-component chromatography column, such proteins can be specifically removed within minutes.

Table 1 below has a list of proteins for which a multi-component antibody affinity matrix (MCAAM) was generated and used to generate a serum sample that consequently contains a protein distribution completely different for these proteins and less abundant proteins which are not otherwise detectable, and becomes visible in the silver-stained gel protein spot patterns in FIG. 3. However, depending on the nature of the proteins to be subtracted, it is not always desirable to pool all matrices into one column body. For many sample applications, at least two separate column bodies are preferred for the reason that proteins may elute from their cognate immobilized antibodies under different specific elution conditions as detailed below.

TABLE 1

| Serum protein Protein ID according to "plasma proteins", Putnam volume IV, 1984 | Relative amount of protein in total serum | Relative amount of affinity matrix in MCAAM |
|---|---|---|
| Albumin | 50 | 48 |
| Immunoglobulin G | 15 | 0* |
| Transferrin | 3.1 | 4 |
| Haptoglobin | 6.8 | 7 |
| Alpha 1 antitrypsin | 3.5 | 5 |
| Alpha 2 macroglobulin | 3.0 | 10 |
| Immunoglobulin A | 3.3 | 5 |
| Immunoglobulin M | 1.9 | 3 |
| Alpha 1 acid glycoprotein | 1.2 | 2 |
| Hemopexin | 1.1 | 3 |
| Alpha 2 HS glycoprotein | 0.8 | 2 |
| Alpha 1 antichymotrypsin | 0.5 | 2 |
| Transthyretin | 0.3 | 1 |
| Apo A1 lipoprotein | 3.0 | 8 |

No immunoaffinity matrix had to be added in for immunoglobulin G, because it is subtracted due to sufficient residual binding by the underivatized protein G and A. Where the residual binding is insufficient, and anti-IgG affinity matrix may be used.

Figure 3:
FIGS. 3A and 3B are images of a silver stained 2-D electrophoresis gels of human serum before, 3A, and after, 3B, immunoaffinity subtraction with a mixture of 14 polyclonal serum protein specific or serum protein family specific chromatographic IgG resins. The X axis shows the pI and the Y axis shows the molecular weight in Kdal.

See FIG. 3 where three specific examples of successful subtraction of serum proteins are shown. Arrows 1-3 point out the protein location in both gels. Thus in gel B, arrow 1 indicates albumin, 2 indicates transferring and 3 indicates haptoglobin chains. Arrows 4 in gel A indicate other major proteins subtracted from serum and do not or in very low amounts appear on gel B. In both gels, about 180 µg serum protein was loaded on IEF gels prior to the 2-D electrophoresis. Essentially no antibody was eluted either before the sample was added or upon elution of sample.

PREPARATIVE EXAMPLE C

Chromatographic Separation

The chromatographic separation of proteins in the present invention uses a chromatography station with column switching valves for at least two columns and separate elution of MCAAM column bound proteins wherein they have different characteristics in terms of their solubilities in elution buffers. Most proteins elute from their cognate antibodies under acid conditions (e.g. 5% acetic acid). Some proteins, however, are not soluble in acidic buffers and may require elution with a chaotropic salt/detergent mixture (2 M urea and 2% CHAPS), some hydrophobic proteins may require organic solvent (e.g.

Figure 2:
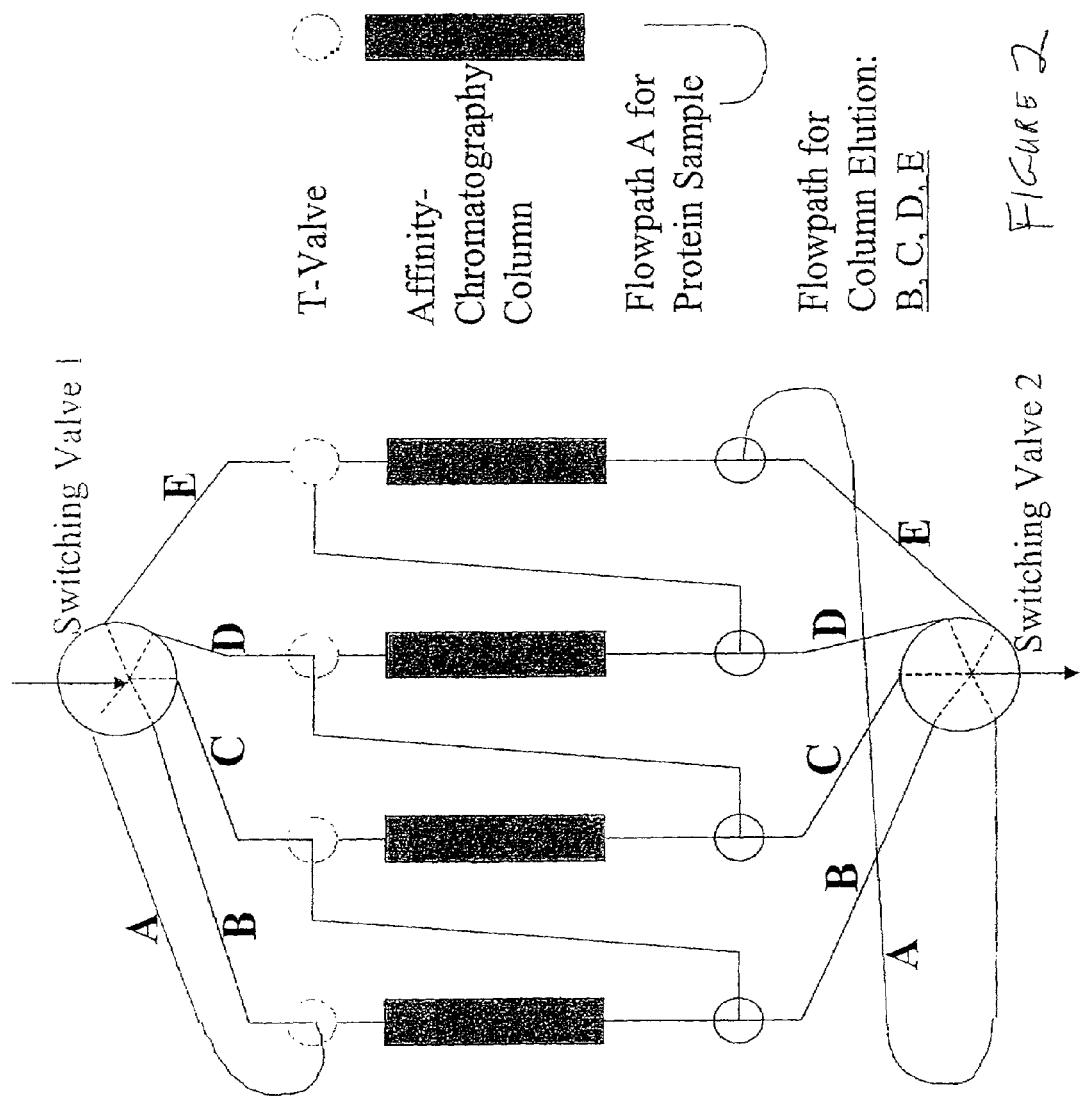
FIG. 2 depicts an arrangement for passing a sample through multiple affinity chromatography columns.

30% acetonitrile) to elute from their cognate antibodies. Thus, in the abovementioned example of serum, alpha-2 macroglobulin and Apo-Al lipoprotein elute more efficiently with the chaotropic salts and buffers containing 20% to 30% organic solvent buffer, respectively. Working with plasma, fibrinogen is more efficiently subtracted when a chaotropic salt buffer is applied for the elution from the immunoaffinity matrix. FIG. 2 shows an example for the combination of the immunosubtraction chromatography system including column switching valves and flow path.

The buffers used were:
a. acid elution buffer: 5% acetic acid, 500 mM NaCl
b. chaotropic salt buffer: 2 M urea, 2% CHAPS, 7% acetic acid
c. organic solvent buffer: 50 mM Tris-HCl pH 7.5, 30% acetonitrile Alternatively, human fibrinogen may be removed by using *Aspergillus fumigatus* conidia as the receptor due to its binding to fragment D or by using the M protein on the surface of group A streptococci.

EXAMPLE D

Combination of Immunoaffinity with Lectin-Affinity Chromatography Generating Two Sets of Protein Samples for 2-DGE In a different embodiment of the present invention, immunoaffinity chromatography was combined with wheat germ agglutinin (WGA) lectin affinity chromatography. Two fractions were generated. In the case of serum as a sample, highly glycosylated proteins, about 30% to 50% of the total protein, were bound by the WGA column and separately eluted with a 0.5 M solution of the sugar N-acetylglucosamine, whereas the second fraction consisted of protein unglycosylated or lacking of affinity for this lectin and thus not bound by the column. The gels in FIG. 4 visualize the set of proteins from serum unbound (a) or bound and eluted from the lectin affinity column with the sugar (b). This fractionation has the purpose to further enrich proteins in either of the two fractions by increasing the protein loading amount for 2-D gel electrophoresis. Using the lectin affinity fractionation procedure, the gain is a nearly two-fold enrichment of unsubtracted serum proteins in two different fractions and a further "pattern simplification" that allows easier analysis upon post-2-DGE gel image acquisition.

Figure 4:
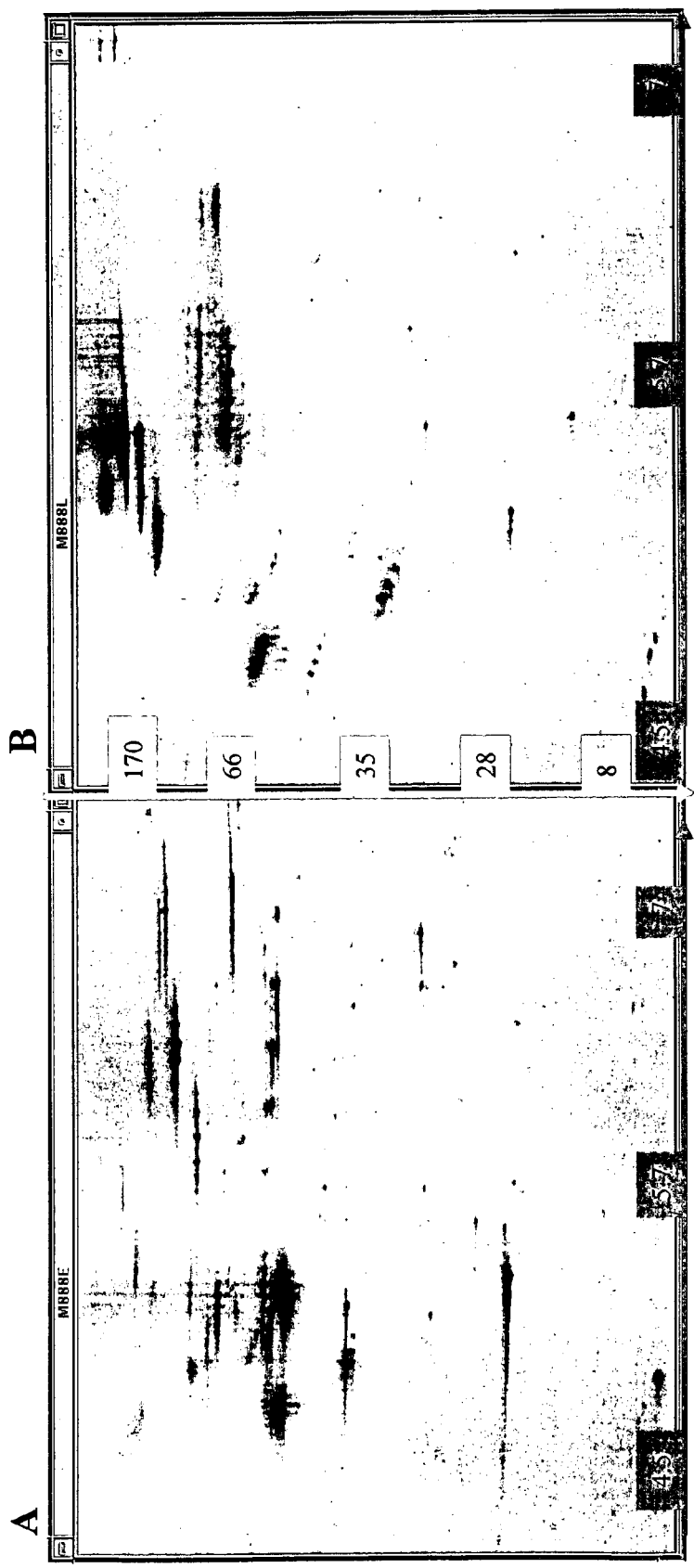
FIGS. 4A and 4B are images of Coomassie Blue G250 stained 2-D electrophoresis gels of human serum after chromatographic immunoaffinity subtraction of 12 serum proteins and fraction of the remaining proteins into a fraction without, 4A, and a fraction with, 4B, lectin affinity. The X-axis shows the pI and the Y-axis shows the molecular weight in Kdal.

In FIG. 4, subtraction of serum proteins was done in the first chromatographic step and remaining proteins were subjected to a strepavidin-derivitized POROS matrix that was further immobilized with biotinylated WGA. In gel A proteins originating from the flowthrough fraction of the column, in gel B proteins from the lectin-bound and 0.5 M N-acetylglucosamine-eluted fraction were analyzed by 2-DGE. In both gels, about 180 µg serum protein was loaded on IEF gels prior to the 2D-electrophoresis.

EXAMPLE E

Sample Preparation for 2-DGE and Analysis

Samples generated by the described immunoaffinity chromatography were diluted during the subtraction process. 3 to 5 mL of subtraction serum protein elutant were collected and concentrated in polysulfone membrane concentration units (Ultrafree 4, from Millipore), equilibrated in 25 mM ammonium bicarbonate, lyophilized, and resolubilized in 9 M urea/2% CHAPS/60 mM DTT buffer a buffer generally used for isoelectric focusing of the proteins in the sample during the first dimension separation of 2-DGE.

Example 1

Matrices carrying antibody that binds six abundant serum proteins were produced. The six proteins were albumin, haptoglobin, transferrin, α-1-antitrysin, $\alpha_2$-macroglobulin and apolipoprotein AI. These proteins were commercially purchased and individually loaded on and bound to a POROS AL matrix. The matrix was packed into a column and commercial polyclonal antibody to each protein was added. The unbound material was discarded. Antibody was eluted, neutralized, desalted and loaded onto a POROS protein A column by the methods mentioned above and as shown in FIG. 1. The antibodies were crosslinked in place by the methods above. Each matrix carrying one type of antibody was tested for binding capacity using known techniques, including exposing graded amounts of a solution of known concentration to the matrix and then determining when no further protein in bound by the matrix. That can be ascertained using known techniques, such as using a UV monitor capable of ascertaining absorbance of the flow through at 280 nm. The binding capacity for each matrix was determined. Then all six types of matrix were mixed in a ratio based on binding capacity of each, which was proportional to the relative amounts of each protein in serum, and loaded into a column.

Serum samples were passed over the column. Sample volumes generally were less than 100 µl in volume. The proteins were washed through with neutral buffer. The eluate was obtained, concentrated and then the proteins therein were separated by 2-DGE. The gels were stained with Coomassie blue and silver stains to reveal the less abundant proteins of serum.

After about ten serum samples loading and elution repeats, a decrease in $\alpha_2$-macroglobulin subtraction was noted. After about 25 serum samples loading and elution repeats, a decline in apolipoprotein AI subtraction also was observed. It is hypothesized that, the acidic aqueous elution buffer (0.8 M acetic acid/0.15 M NaCl) to detach and/or to solubilize a $\alpha_2$-macroglobulin and apolipoprotein $A_1$ was insufficient or destabilizing. The two proteins appeared to remain associated with the antibody matrix or may have precipitated after release from the antibody on the matrix. The capacity of the column to completely subtract albumin, haptoglobin, transferrin and α-1-antitrypsin was close to the amounts of proteins found in 62.5 µL serum. A two column system where anti-$\alpha_2$-macroglobulin and anti-apolipoprotein AI are present on a separate column with the following buffers were used. It was determined that $\alpha_2$-macroglobulin could be eluted from the matrix with 1.5 M ammonium thiocyanate and apolipoprotein AI with 30% acetonitrile in aqueous 0.15 M NaCl.

Example 2

Post-fractionation protein samples in 500 mM ammonium bicarbonate (AmBic) were concentrated over ultrafiltration membranes. The AmBic concentration was diluted to 25 mM AmBi, the sample was transferred into a lyophilization vial, 6 µL of 2 M sucrose were added, and the sample was lyophilized for at least 48 h. An hour before applying the sample to the isoelectric focusing unit tube gel, the sample was resolubilized in Pink Mix (9M urea, 2% CHAPS (a commercially available buffer), 0.5% DTT and 2% ampholytes (pH 8-10.5)) and checked for complete solubility. Those samples were used in 2-DG electrophoresis following the procedure of Anderson et al, Electrophoresis, 12: 907-930 (1991).

Example 3

Neuraminidase is efficient in collapsing some protein (glycosylation) trains. A small amount of neuraminidase is sufficient to reduce spot complexity and to improve the intensity of specific spots. About 25 mUnits of neuraminidase (Prozyme, sialidase A) were sufficient to eliminate the most obvious glycosylation trains in the equivalent of one 2-D serum protein loading aliquot following a 90 minute digest. Deglycosylation should be complete to enable useful protein spot comparisons. Because Prozyme enzyme is recombinant, contaminating proteases are absent.

Example 4

Resolution of plasma proteins is worse in plasma than proteins are in tissues primarily because of the abundant fibrinogen chains in the gels. A polyclonal anti-fibrinogen matrix was generated by the method of Example 1. Binding specificity and capacity were satisfactory to enable subtractions of fibrinogen.

Example 5

Figure 5:
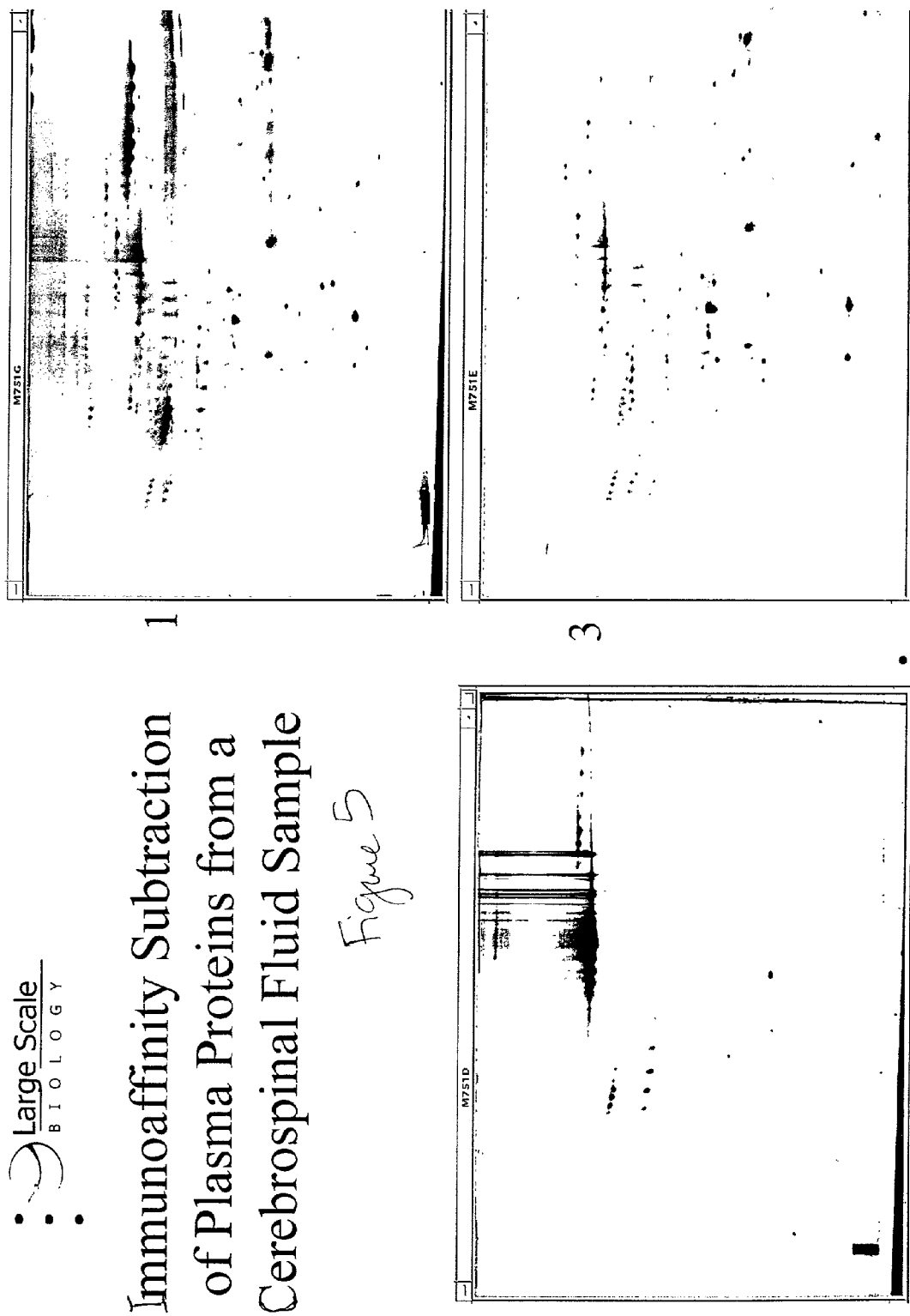
FIGS. 5(1), 5(2) and 5(3) are images of Coomassie Blue G250 stained 2-D electrophoresis gels of human cerebral spinal fluid before chromatographic immunoaffinity subtraction, the column retained proteins and the flow-through proteins.

A column carrying plural antibodies to subtract abundant proteins found in serum was used with cerebrospinal fluid. The major difference from serum is the significantly higher loading volume for a chromatographic separation (1.2 mL as compared to 62 µL for serum) because of the lower protein amounts in cerebrospinal fluid. Even though the column was not optimized for cerebrospinal fluid, it preformed well. A comparison by 2-DE of CSF sample proteins with and without the immunosubtraction procedure is shown in FIG. 5. Many low abundance protein spots are visible in the immunosubtracted sample 2-DG, which are not observable in the whole sample 2-DG.

Example 6

Protein subtraction columns were prepared to remove common proteins that comprise most of the protein in the sample. Serum was obtained from about 80 pairs of monozygotic twins. The serum samples contain about 70 mg/ml of protein. Lipids were found not to interfere with the chromatographic separations. Twenty-five to fifty microliter serum samples were used.

For some samples, two columns were used. The first column contained POROS beads to which was bound antibodies directed to albumin, transferrin and haptoglobin (ATH column). The antibodies were bound to the matrix by protein A, protein G or a mixture of the two followed by crosslinking as above. The second column contained immobilized wheat germ agglutinin.

For other samples, the first column contained antibody specific for $\alpha_1$-antitrypsin, albumin, transferrin and haptoglobin (AATH column). The second column comprised immobilized protein A. All antibodies were crosslinked to the protein A or protein G using the method of Schneider et al., J. Biol. Chem. 257:10766-10769, 1982. Approximately 4 ml of affinity resin were used. Generally, the columns removed all of the selected components.

As indicated above, about 1.7 to 3.4 mg of protein was added to the first column. In the case of the ATH column, unbound protein was eluted using 0.5 M ammonium bicarbonate buffer and then transferred to the second column. A first unbound fraction was eluted with the 0.5 M ammonium bicarbonate buffer and then a second fraction was eluted using 0.5 M N-acetylglucosamine followed by 0.5 M ammonium bicarbonate. UV readings at 280 nm were monitored to control for reproducibility and column performance. Proteins retained on the column were removed from the ATH column using a pH 2.5 acetic acid buffer to regenerate the column.

About half of the serum protein was removed from the sample by this procedure. The first sample contains glycosylated proteins. The second sample that was passed over the lectin column contains non-glycosylated proteins. The final protein concentrations ranged between 12 and 22 mg/ml in 0.5 M ammonium bicarbonate buffer. The fractions were concentrated, the buffer was exchanged and then the sample was lyophilized.

The samples were resolubilized in a buffer comprising 9 M urea, 2% CHAPS (a commercially available buffer), 0.5% DTT and 2% ampholytes (pH 8-10.5) and 5-20 µl samples were loaded onto 2-D gels. The sample proteins were separated in an ISO-DALT system as known in the art and per example 2 above. The resulting Coomassie stained gels were scanned and digitized in red light at 133 µm resolution and the images were processed using the Kepler system as known in the art. The patterns of proteins found on each gel were almost completely different from each other.

The gels were destained then silver stained. Images were taken at 30-second intervals and the development was stopped using 88 g tris in 2 L of deionized water and 44 ml of glacial acetic acid in accordance with the methods described in WO 01/16884.

The samples first run over the AATH column were treated in a similar fashion. The gels were compared to ascertain correlation of proteins with particular disease states, such as obesity, diabetes, osteoporosis, osteoarthritis and hypertension between the twin pairs.

Example 7

The method of Example 1 was repeated except for using antibody matrixes to 12 and 14 antigens as given in Table I. A comparison of 2-DG of sample proteins with and without the immunosubtraction procedure is shown in FIG. 4. Many low abundance protein spots are visible in the immunosubtracted sample 2-DG, which are not observable in the whole sample 2-DG.

Example 8

Figure 6:
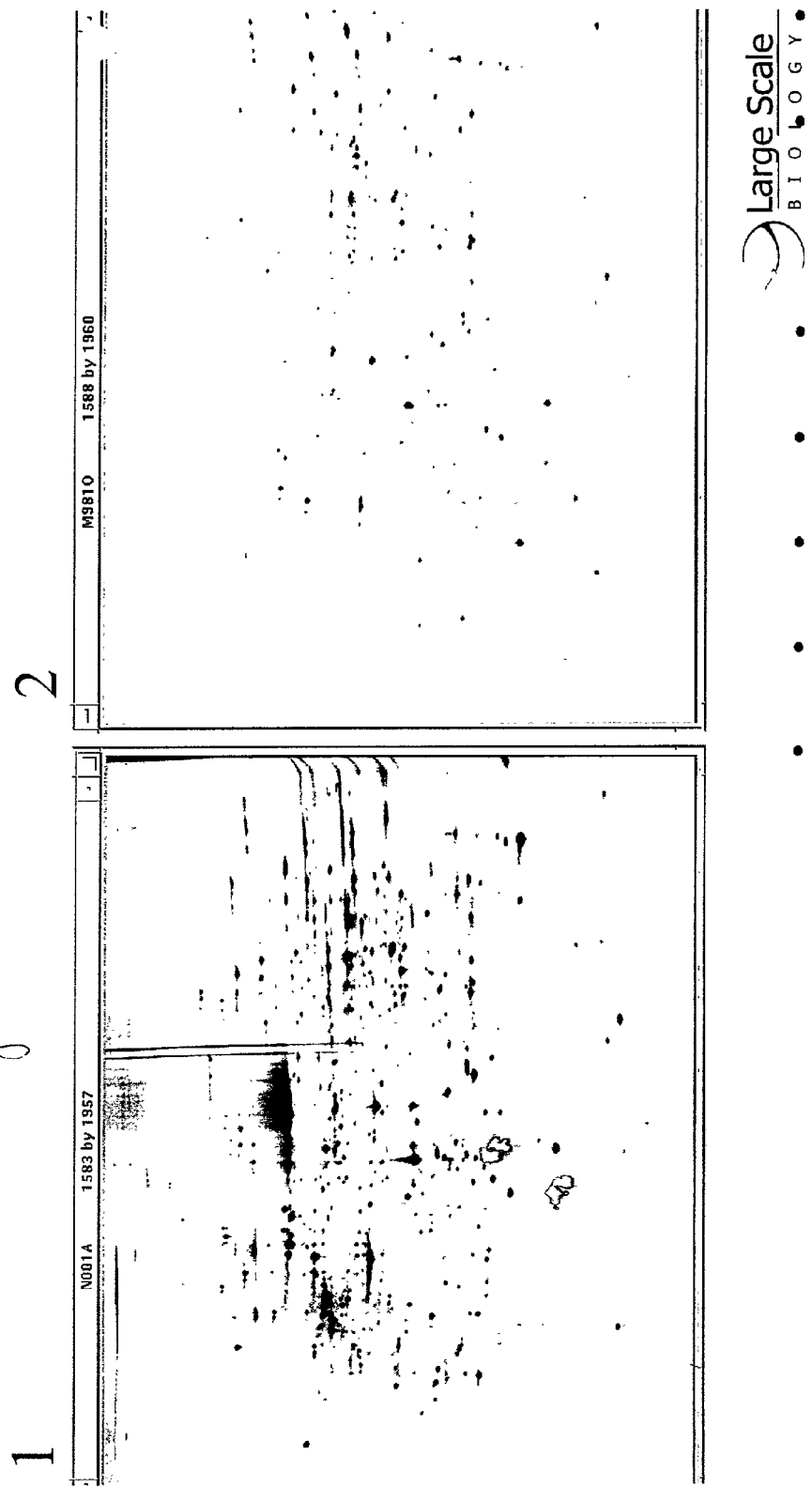
FIGS. 6 (1) and (2) are images of Coomassie Blue G250 stained 2-D electrophoresis gels of soluble protein fraction of kidney cortex tissue before and after chromatographic immunoaffinity subtraction.

The method of Example 1 was repeated except for using antibody matrixes to serum and blood proteins. A comparison by 2-DE of kidney cortex tissue protein fraction with and without the immunosubtraction procedure is shown in FIG. 6. Many low abundance protein spots are visible in the immunosubtracted sample 2-DG, which are not observable in the whole sample 2-DG.

Example 9

The method of Example 1 was repeated except for using antibody matrixes to albumin and alpha acid glycoprotein. A comparison by 2-DE of urine sample proteins with and without the immunosubtraction procedure is shown in FIG. 7. Many low abundance protein spots are visible in the immunosubtracted sample 2-DG, which are not observable in the whole sample 2-DG.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

We claim:

1. A method for producing and recovering a modified sample, said method comprising:

removing at least a first protein and a second protein from a sample, said removing step comprising contacting said sample with an affinity binding composition comprising a first solid phase matrix with a first receptor immobilized thereon capable of specific binding to said first protein but not said second protein and a second solid phase matrix with a second receptor immobilized thereon capable of specific binding to said second protein but not said first protein, wherein each said solid phase matrix is a plurality of particles and said first and second solid phase matrices are present as a mixture in said binding composition;

so that when said sample is contacted with said affinity binding composition, said first protein present in said sample binds to said first receptor present on said first solid phase matrix such that said first protein is removed from said sample and said second protein present in said sample binds to said second receptor present on said second solid phase matrix such that said second protein is removed from said sample and said modified sample is thereby produced, wherein said modified sample is not bound by a solid phase matrix; and recovering said modified sample.

2. The method of claim 1, wherein at least 50% by weight of all proteins in the sample are removed.

3. The method of claim 1, further comprising the step of analyzing a plurality of proteins remaining in the modified sample.

4. The method of claim 1, wherein at least one of the proteins is present at higher abundance than at least one of the plurality of proteins remaining in the sample after removal of the proteins.

5. The method of claim 1, wherein the affinity binding composition further comprises:

a third receptor immobilized on a third solid phase matrix, capable of specific binding to a third protein but not the first protein or the second protein.

6. The method of claim 5, wherein the third solid phase matrix contacts the first and second solid phase matrices.

7. The method of claim 1, wherein the affinity binding composition further comprises:

a fourth receptor immobilized on a fourth solid phase matrix, capable of specific binding to a fourth protein but not the first protein, the second protein or the third protein.

8. The method of claim 7, wherein the fourth solid phase matrix contacts the first, second, and third solid phase matrices.

9. The method of claim 8, wherein the affinity binding composition further comprises:

a fifth receptor immobilized on a fifth solid phase matrix, capable of specific binding to a protein but not the first protein, the second protein, the third protein or the fourth protein.

10. The method of claim 9, wherein the fifth solid phase matrix contacts the first, second, third, and fourth solid phase matrices.

11. The method of claim 1, wherein the receptors are antibodies or antibody fragments that specifically bind to the proteins.

12. The method of claim 1, wherein the receptors are recombinantly produced.

13. The method of claim 1, wherein at least one of the proteins is selected from the group consisting of: immunoglobulins, albumin, transferrin, haptoglobin, $\alpha_1$-antitrypsin, hemopexin, $\alpha_1$-acid glycoprotein, $\alpha 2$ HS glycoprotein, myosin, transthyretin, $\alpha_1$-antichymotrypsin, apolipoprotein Al, $\alpha_2$-macroglobulin, fibrinogen, and prealbumin, and combinations thereof.

14. The method of claim 1, wherein at least two of the proteins are selected from the group consisting of: immunoglobulins, albumin, transferrin, haptoglobin, $\alpha_1$-antitrypsin, hemopexin, $\alpha_1$-acid glycoprotein, $\alpha 2$ HS glycoprotein, myosin, transthyretin, $\alpha_1$-antichymotrypsin, apolipoprotein Al, $\alpha 2$-macroglobulin, fibrinogen, and prealbumin.

15. The method of claim 1, wherein at least three of the proteins are selected from the group consisting of: immunoglobulins, albumin, transferrin, haptoglobin, $\alpha_1$-antitrypsin, hemopexin, $\alpha_1$-acid glycoprotein, $\alpha 2$ HS glycoprotein, myosin, transthyretin, $\alpha_1$-antichymotrypsin, apolipoprotein Al, $\alpha_2$-macroglobulin, fibrinogen, and prealbumin.

16. The method of claim 1, wherein at least four of the proteins are selected from the group consisting of: immunoglobulins, albumin, transferrin, haptoglobin, $\alpha_1$-antitrypsin, hemopexin, $\alpha_1$-acid glycoprotein, $\alpha 2$ HS glycoprotein, myosin, transthyretin, $\alpha 1$-antichymotrypsin, apolipoprotein Al, $\alpha_2$-macroglobulin, fibrinogen, and prealbumin.

17. The method of claim 1, wherein at least three proteins are removed from a sample.

18. The method of claim 1, wherein at least four proteins are removed from a sample.

19. A method for producing and recovering a modified sample, said method comprising:

removing at least a first protein and a second protein from a sample, said removing step comprising contacting said sample with an affinity binding composition comprising a plurality of solid phase matrices with a plurality of receptors having different protein binding specificities immobilized thereon such that each solid phase matrix has a different protein binding specificity, wherein each said solid phase matrix is a plurality of particles and said plurality of solid phase matrices are present as a mixture in said binding composition, so that when said sample is contacted with said affinity binding composition, said at least two proteins become bound to said affinity binding composition and said proteins are thereby removed from the sample such that the modified sample is produced, wherein said modified sample is not bound by a solid phase matrix; and recovering said modified sample.

20. The method of claim 1, or 19, wherein the sample is passed through a column containing the affinity binding composition to produce the modified sample, wherein the affinity column has a fluid inlet and a fluid outlet, and wherein the modified sample is collected at the fluid outlet.

21. The method of claim 19, wherein at least three proteins are removed from a sample.

22. The method of claim 19, wherein at least four proteins are removed from a sample.

* * * * *

UNITED STATES PATENT AND TRADEMARK OFFICE
CERTIFICATE OF CORRECTION

PATENT NO.       : 7,691,645 B2                                    Page 1 of 1
APPLICATION NO.  : 09/977358
DATED            : April 6, 2010
INVENTOR(S)      : N. Leigh Anderson et al.

It is certified that error appears in the above-identified patent and that said Letters Patent is hereby corrected as shown below:

In column 22, line 18, in claim 14, delete "α2" and insert -- $\alpha_2$ --, therefor.

In column 22, line 29, in claim 16, delete "α1" and insert -- $\alpha_1$ --, therefor.

Signed and Sealed this

Twentieth Day of July, 2010

David J. Kappos
*Director of the United States Patent and Trademark Office*